United States Patent [19]
Crow et al.

[11] Patent Number: 5,234,953
[45] Date of Patent: Aug. 10, 1993

[54] TREATMENT OF CONGESTIVE HEART FAILURE

[75] Inventors: James W. Crow, Raleigh; Walker A. Long, Chapel Hill, both of N.C.

[73] Assignee: Burroughs Wellcome Co., Research Triangle Park, N.C.

[21] Appl. No.: 705,049

[22] Filed: May 23, 1991

[30] Foreign Application Priority Data

May 24, 1990 [GB] United Kingdom ............ 9011588

[51] Int. Cl.⁵ .................... A61K 31/19; A61K 31/557
[52] U.S. Cl. ...................................... 514/573; 514/530
[58] Field of Search .................. 514/573, 519

[56] References Cited

U.S. PATENT DOCUMENTS

| | | | |
|---|---|---|---|
| 4,306,075 | 12/1981 | Aristoff | 560/56 |
| 4,680,288 | 7/1987 | Irmscher et al. | 514/63 |
| 4,971,987 | 11/1990 | Vorbrueggen et al. | 514/374 |
| 5,013,758 | 5/1991 | Skuballa et al. | 514/573 |
| 5,028,628 | 7/1991 | Tadepalli et al. | 514/573 |
| 5,153,222 | 10/1992 | Tadepalli et al. | 514/571 |

FOREIGN PATENT DOCUMENTS

0347243A1 12/1989 European Pat. Off. .
0458641A2 11/1991 European Pat. Off. .

OTHER PUBLICATIONS

Riegger A. J. G., Neurohumoral vasoconstrictor systems in heart failure, Eur. Heart J. 6: pp. 479-489, 1985.
Packer M., Neurohumoral interactions and adaptations in congestive heart failure, Circulation 77: pp. 721-730, 1986.
Dzau, V. J., Packer, M., Lilly, L. S., Swartz, S. L., Hollenberg, N. K., Williams G. H., Prostaglandins in severe congestive heart failure. Relation to activation of the renin-angiotensin system and hyponatremia, N. England J. Med. 310: pp. 347-352, 1984.
Punzengruber, E., Stanek, B., Sinzinger H., Silbertbauer, F., Bicyclo-prostaglandin $E_2$ metabolites in congestive heart failure and relation to vasoconstrictor neurohumoral principles, Am. J. Cardiol 57: pp. 619-623, 1986.
Yui, Y., Nakajama, H., Kawai, C., Murakami, T., Prostacyclin therapy in patients with congestive heart failure, Am. J. Cardiol. 50: pp. 320-324, 1982.
Auingor O., Virgolini, I., Weissel, M., Bergmann, H., Sinzinger, H., Prostacyclin $I_2$ ($PGI_2$) increases left ventricular ejection fraction (LVEF), Prosinglandine 36: pp. 149-254, 1989.

(List continued on next page.)

Primary Examiner—Leonard Schenkman
Attorney, Agent, or Firm—Donald Brown; Robert T. Hrubiec; Lawrence A. Nielsen

[57] ABSTRACT

The present invention is concerned with the use of a compound of formula (I)

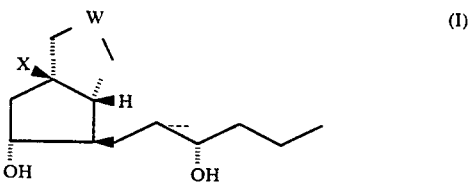

wherein
—W— is

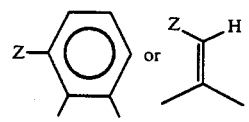

wherein Z is $-V(CH_2)_bCO_2H$ where b is 1 or 2 and V is oxygen when b is 1 or methylene when b is 2;
X is hydrogen, cyano, or $-C\equiv CH$; and
the dotted line represents an optional double bond; and physiologically functional derivatives thereof, in the treatment of congestive heart failure.

8 Claims, No Drawings

OTHER PUBLICATIONS

Yui, Y., Sakurai, T., Nakajina, H., Kawai, E., Effect of prostacyclin and prazocin in the treatment of congestive heart failure, with special reference in the sympathetic nervous system, Jpn. Circulation J., pp. 365–372, 1984.

Awan, N. A., Evenson, M. K., Needham, K. E., Beattie, J. M. Armsterdam, E. A., Mason T. T., Cardiocirculatory and myocardial energic effects of prostaglandin $E_1$ in severe left ventricular failure due to chronic coronary disease, Am. Heart J., 102: pp. 703–709, 1981.

Popat, K. D., Pitt, B. P., Hemodynamic effects of prostaglandin $E_1$ in patients with acute myocardial infarction and left ventricular failure. Am. Heart J. 103: pp. 485–489, 1982.

Jacobs, P., Naeije, R., Renard, M., Melot, C., Mois, P., Hallemmans, R., Effects of prostaglandin $E_1$ on hemodynamic and blood gases in severe left heart failure, J. Cardiovascular Pharmacol. 5: pp. 170–172, 1983.

Yui, Y., Takatsur, Y., Hattori, R., Susawa, T., Sakaguchi, K., Yui, N., Kawai, C., Vasodilator therapy with a new stable prostacyclin analog, OP–41483, for congestive heart failure due to coronary artery disease and comparision of hemodynamic effects and platelet aggregation with nitroprusside, Am. J. Cardiol. 58: pp. 1042–1045, 1986.

Elsner D. Kramer EP, Riegger AJG. Hemodynamic, humoral, and renal effects of the prostacyclin analogue iloprost in conscious dogs with and without heart failure, J. Cardiac Pharmacol 16: pp. 601–608, 1990.

Radernacher, P., Santak, B., Wust, H. J., Tarnow, J., Falke, J. Prostacyclin for the treatment of pulmonary hypertension in the adult respiratory distress syndrome: Effects on pulonary capillary pressure and ventilation-perfusion distributions. Anesthesiology 72: pp. 238–244, 1990.

Rubin, L. J., Mendoza, J., Hood, M., et al., Treatment of primary pulmonary hypertension with continuous intravenous prostacyclin (Epoprostenol), Results of a randomized trial. Annals Internal Medicine 112: 485–491, 1990.

Malik, K. U., Weis M. T., Jaiswal, N., Mechanism of action of adrenergic and cholinergic stimuli on cardiac prostaglandin, synthesis; pp. 327–330 In: Advances in Prostaglandin, Thromboxane, and Leukotriene Research, vol. 19 ed (B. Samulsson, PY.-K. Wong, F. F. Sun eds) Raven Press, Ltd., New York, 1989.

Omini, C., Daffonchio, L., Abbraccho, M. P., Cattabeni, F., Berti, F., Beta adrenoceptor desensitization in lung: A role for prostagiandins. pp. 524–527 In: Advances in Prostaglandin, Thromboxane, and Leukotriene Research, vol. 19 ed (B. Samuelsson, PY.-K. Wong, F. F. Sun eds), Raven Press, Ltd., New York, 1989.

Zusman R. M., Crow, J. W., Cato, A. E., Talkoff-Rubin N., Effects of prostacyclin infusion in uremic patients; Hematologic and hemodynamic response. Clin. Pharmaco. Ther 30: 251–257, 1981.

Olivari, M. T., Levine, T. B., Goldenbert, I. F., Cohn, J. N., Hemodynamic consequences of prostaglandin $E_2$ activation of the renin–angiotensin system in heart failure, pp. 437–439 In: Advances in Prostacyclin, Thromboxane and Leukotriene, vol. 17 ed (B. Samuelsson, R., Paoletti, R. W., Ramwell eds) Raven Press, New York, 1987.

Dzau, V. J., Vascular and renal prostaglandin as counter-regulatory system in heart failure, European Heart Journal 9 (Suppl. H) pp. 15–19, 1988.

FitzFerald, G. A., Hossmann, V., Hummerich, W., Konrads, A., the renin–kallikrein–prostaglandin system; plasma active an inactive renin and urinary kallikrein during prostaglandin infusion in man, Prostaglandins and Medicine 5: pp. 445–456, 1980.

Fitzpatrick, T. M., Alter, I., Corey, E. J., Ramwell, E. J., Rose, J. C., Kot, P. A., Cardiovascular responses to PGI in the dog, Circ. Res. 42: pp. 192–194, 1978.

Dusting, G. J., Moncada, S., Vane, J. R., Prostaglandins, their intermediates and precursors; Cardiovascular actions and regulatory rates in normal and abnormal circulatory systems, Prigress in Cardiovascular Diseases 21: pp. 405–426, 1979.

Jentzer, J. H., Sonnerblick, E. H., Kirk, E. S., Coronary and systemic vasomotor effects of prostacyclin: implications for ischemic myocardium, pp. 323–338 In: Prostacyclin (J. R. Vane, S. Bergstrom eds) Raven Press, New York, 1979.

FitzGerald, G. A., Dargie, H. J., Watkins, J., Brown, M. J., Friedman, L. A., Lewis, P. J., Cardiac effects of prostacyclin in man, pp. 145–151 In: Clinical Pharmacology of Prostacyclin (P. J. Lewis, J. O'Grady eds) Raven Press, New York, 1981.

R. Berkow et al., "The Merck Manual of Diagnosis and Therapy", 15th edition, 1987, pp. 415–429, MSD Re- (List continued on next page.)

OTHER PUBLICATIONS search Laboratories, Rahway, U.S., pp. 423-429.
Prostaglandins, Leukotrienes and essential fatty acids, vol. 43, No. 4, Aug. 1991, pp. 277-286, GB; R. P. Steffen et al.: "The effects of 15-AU81 a chemically stable prostacyclin renin-angiotensis systems of anesthetized dogs".
Walker A. Long and Lewis J. Rubin, Prostacyclin and PGE, Treatment of Pulmonary Hypertension; Am. Rev. Respir. Dis., 1987; 136; pp. 773-776.
American Heart Journal; Oct. 1984, vol. 108, No. 4, part 1; Siegel et al.
Hemodynamic effects of prostaglandin $E_1$, et al., 1982, The C. V. Mosby Co., $PGE_1$ hemodynamic effects in AMI with CHF; Popat and Pitt et al., pp. 485-489.
Effects of prostaglandin $E_1$ on Hemodynamics and blood in severe heart failure, Journal of Cardiovascular Pharm. 5: pp. 170-171, 1983 Raven Press, New York.
PGE, Therapy of Severe CHF in CHAD; Awan et al., pp. 703-709, 1981.
Effects of Prostacyclin on the Contractile Performance of Cardiac Muscle (1); Arch. Int. Pharm., 256, pp. 161-162, 1982.
Effect of Prostacyclin on Vascular Capacity in the Dog, Fulghum et al., The American Society for Clin. Inv., Inc., vol. 76, pp. 999-1006; 1985.
Effective of Prostacyclin and Prazosin in the Treatment of Congestive Heart Failure; with Special Reference on the Sympathetic Nervous System, Yoshiki Yui et al., Jap. Circ. Journal, vol. 48, 1984.
Newman et al., Increased Myocardial Release of Prostacyclin in Dogs with Heart Failure, J. Cardiovascular Pharmacol. 5:194-201 (1983).
Yui, et al., Prostacyclin Therapy in Patients with Congestive Heart Failure, Amer. J. Cardiol. 50:320-324 (1982).
Stanek et al., Increase in Bicycloprostaglandin E2 Metabolite in Congestive Heart Failure in Response to Captopril, Clin. Cardiol., 12(2):97-101 (1989).
Elsner et al., Hemodynamic, Hormonal and Renal Effects of the Prostacyclin Analogue Iloprost in Conscious Dogs with and without Heart Failure, J. Cardiovasc. Pharmacol., 16(4):601-608 (1990).
Long et al., Prostacyclin and PGE, Treatment of Pulmonary Hypertension 1,2 Am. Rev. Respir. Dis., 136:773-776 (1987).
Berkow, et al., ed., Diseases of the Heart and Pericardium from the Merck Manual of Diagnosis and Therapy, 15th Edition, pp. 415-429 (1987).
Sprague et al., Differential Response of the Pulmonary Circulation to Prostaglandins E2 and F2a in the Presence of Unilateral Alveolar Hypoxia, J. Pharmacol. and Exp. Therap. 229:38-43 (1984).
Prostacyclin Therapy in Patients With Congestive Heart Failure, Yoshiki Yui, et al., The American Journ. of Cardiology; vol. 50; August 1982.
Rubin et al., Prostacyclin-induced Acute Pulmonary Vasodilation in Primary Pulmonary Hypertension, Circulation 66:334-338 (1982).
Soifer et al., The Development Effects of Prostaglandin D2 on the Pulmonary and Systemic Circulations in the Newborn Lamb, J. Develop. Physiol., 5:237-250 (1983).
Aristoff et al., Synthesis and Structure-Activity Relationships of Benzindene Prostaglandins: Novel Potent Antiulcer Agents, 275-277 (1985).
Chand et al., Differential Effects of Prostaglandins on Canine Intrapulmonary Arteries and Veins, Pharmacol. 73:819-827 (1981).
Angerio et al., Cardiovascular Responses to PDG2 in Dog (39943), Proc. Soc. Exp. Biol. and Med., 156:393-395 (1977).
Grossman et al., Pulmonary Hypertension, Abnormalities of Circulatory Function, 835-851.

TREATMENT OF CONGESTIVE HEART FAILURE

The present invention is concerned with the treatment of congestive heart failure (CHF).

CHF is a clinical syndrome characterized by a limitation of exercise tolerance due to dyspnea and/or fatigue which can be attributed to an abnormality of cardiac function. Such cardiac dysfunction may be secondary to alterations in cardiac filling or cardiovascular transport (or both) and can be associated with identifiable changes in systolic and diastolic function which may lead to pulmonary hypertension.

U.S. Pat. No. 4,306,075 describes novel benzindene prostaglandins which produce various pharmacological responses, such as inhibition of platelet aggregation, reduction of gastric secretion and bronchodilation. It is indicated that these compounds have useful application as anti-thrombotic agents, anti-ulcer agents and anti-asthma agents. There is no suggestion or disclosure that they may be used in the treatment of any type of CHF. Structure activity relationships of benzindene prostaglandins have also been described (P. A. Aristoff, A. W. Harrison, P. D. Johnson, and A. Robert, Advances in Prostaglandin, Thromboxane, and Leukotriene Research, Vol. 15, edited by O. Hayaishi and S. Yamamoto. Raven Press, New York, 1985., Pg. 275-277).

European Patent Specification 0347243 describes a class of benzindene and non-benzindene prostaglandins suitable for use in the prophylaxis, treatment and diagnosis of pulmonary hypertension and Raynaud's disease. We have identified a sub-class of the compounds described in European Patent Specification 0347243(as well as U.S. Ser. No. 07/367,090) which have potent systemic and pulmonary vascular effects which render them suitable for use in the treatment of CHF.

The present invention, therefore, lies in the use of a compound of formula (I)

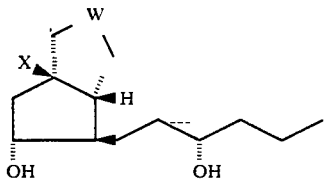

(I)

wherein
—W— is

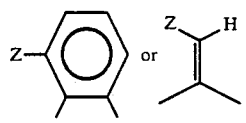

where Z is —V(CH$_2$)$_b$CO$_2$H where b is 1 or 2 and V is oxygen when b is 1 or methylene when b is 2;
X is hydrogen, cyano, or —C≡CH; and
the dotted line represents an optional double bond;
and physiologically acceptable base salts, esters and other physiological functional derivatives thereof, for the treatment of congestive heart failure.

The term "physiological functional derivative" is used herein to denote a bioprecursor or "prodrug" which may be converted to a compound of formula (I) in-vivo, for example, an amide wherein the amide nitrogen is optionally substituted by one or two C$_{1-4}$ alkyl groups.

All references hereinafter to "a compound of formula (I)" include references to its physiologically acceptable base salts, esters, and other physiological functional derivatives.

The present invention further lies in the use of the compounds of the present invention in the treatment of CHF which is accompanied by pulmonary hypertension.

In animal tests, compounds of formula (I) are potent pulmonary vasodilators and markedly attenuate the pulmonary vasoconstriction induced by hypoxia. The overall acute beneficial hemodynamic effects observed are substantial reductions in pulmonary vascular resistance, pulmonary arterial pressure, systemic vascular resistance and mean arterial blood pressure and increases in cardiac output and stroke volume. All of these effects are desirable in the treatment of CHF.

In normotensive (i.e., absence of any indication of pulmonary or systemic hypertension) dogs, administration of an ACE-inhibitor, a cardiotonic, or a diuretic, either simultaneously with or immediately prior to, the administration of a compound of formula (I) respectively blocks, attenuates, and potentiates the increase in Angiotensin II plasma concentration induced by the compounds of formula (I) without significantly affecting its hemodynamic profile. Pre-treatment with an ACE-inhibitor also enhanced the cardiovascular effects of the compounds of formula (I). However, it is not considered advisable to administer the compounds of formula (I) with a diuretic in the absence of an ACE-inhibitor and/or a cardiotonic. Preferred compounds for co-administration with a compound of formula (I) include the ACE-inhibitors enalapril, captopril, and linsinopril; the cardiotonic digoxin; and the diuretics forosemide and butemenide.

The compounds of the present invention can be administered as either an acute treatment or a chronic treatment for CHF. The preferred methods of administration of the compounds of the invention are via transdermal delivery or intravenous injection.

According to a further aspect of the invention, therefore, there is also provided a method for the treatment of CHF in a mammal, such as a human, which comprises the administration of a therapeutically effective amount of a compound of formula (I).

Preferred compounds of formula (I) having particularly advantageous properties in respect of the treatment of CHF are (1R,2R,3aS,9aS)-([2,3,3a,4,9,9a-hexahydro-2-hydroxy-1-((S)-3-hydroxyoctyl)-1H-benz[f]inden-5-yl]oxy)acetic acid (which is also known as [1R-(1α(S*)-,2α,3aα,9aα)]-([2,3,3a,4,9,9a-hexahydro-2-hydroxy-1-(3-hydroxyoctyl)-1H-benz-[f]inden-5-yl]oxy)acetic acid or 9-deoxy-2',9-methano-3-oxa-4,5,6-trinor-3,7-(1',3'-interphenylene)-13,14-dihydro-prostaglandin F$_1$) having formula (A), (5Z,9R)-9-cyano-6a-carbaprostaglandin I$_2$ (B), and (5Z,9R)-9-ethynyl-6a-carbaprostaglandin I$_2$ (C) which have the following structures:

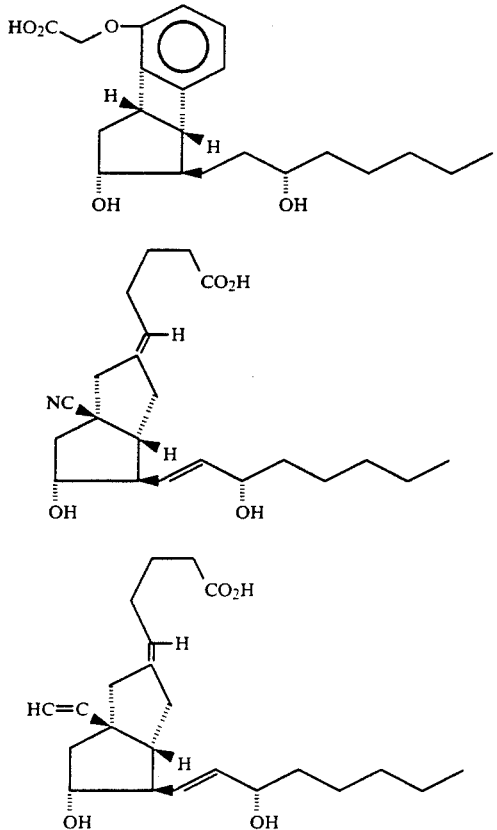

and physiologically acceptable base salts, esters and other physiologically functional derivatives of any thereof.

Of these preferred compounds of formula (I), compound (A) and its physiologically acceptable base salts, esters and other physiologically functional derivatives are particularly preferred, especially compound (A) itself of formula (I) wherein

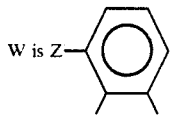

Z is —CH$_2$CO$_2$H
X is H.

Base salts in accordance with the invention include ammonium salts, alkali metal salts such as those of sodium and potassium, alkaline earth metal salts such as those of calcium and magnesium, salts with organic bases such as dicyclohexylamine and N-methyl-D-glutamine, and salts with amino acids such as arginine and lysine.

The amount of a compound of formula (I), which is required for the treatment of CHF will depend on a number of factors, in particular the nature and severity of the condition being treated and the preferred mode of administration, and the condition of the patient. In general, a daily dose for the treatment of CHF is in the range 25 ug to 250 mg, typically from 1.0 ug to 0.05 mg, per day per kilogram bodyweight. For example, an intravenous dose may be in the range 0.5 ug to 1.5 mg/kg/day, which may conveniently be administered as an infusion of from 0.5 ng to 1.0 ug per kilogram per minute. Infusion fluids suitable for this purpose may contain, for example, from 10 ng to 10 ug per milliliter of the active compound. Ampoules for injection may contain, for example, from 0.1 ug to 1.0 mg and orally administrable unit dose compositions, such as tablets or capsules, may contain, for example, from 0.1 to 100 mg, typically from 1 to 50 mg. In the case of physiologically acceptable salts, the weights indicated above refer to the weight of the active compound ion, that is, the ion derived from the compound of formula (I).

The ACE-inhibitors, cardiotonics and diuretics to be used in accordance with the present invention are administered via the accepted routes and in the accepted dosages.

The manufacture of a pharmaceutical composition in accordance with the invention typically involves admixing a compound of formula (I) or one of its physiologically acceptable salts with one or more carriers and/or excipients. The latter must, of course, be acceptable in the sense of being compatible with any other ingredients in the composition and must not be deleterious to the patient. The carrier may be a solid or a liquid, or both, and is preferably formulated with the active compound as a unit-dose composition, for example, a tablet, which may contain from 0.05% to 95% by weight of the active compound. The compounds of formula (I) may be incorporated in the compositions of the invention by any of the well known techniques of pharmacy consisting essentially of admixing the components.

The compositions of the invention include those suitable for oral, buccal (e.g. sub-lingual), parenteral (e.g. subcutaneous, intramuscular, intradermal, and intravenous), rectal, topical, transdermal, nasal and pulmonary administration, although the most suitable route in any given case will depend on the nature and severity of the condition being treated.

Compositions suitable for oral administration may be presented in discrete units adapted for instant or controlled release such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. Such compositions may be prepared by any suitable method of pharmacy which includes the step of bringing into association the active compound and a suitable carrier (which may contain one or more accessory ingredients). In general, the compositions of the invention are prepared by uniformly and intimately admixing the active compound with a liquid or finely divided solid carrier, or both, and then, if necessary, shaping the resulting mixture. For example, a tablet may be prepared by compressing or moulding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Compositions suitable for buccal (sub-lingual) administration include lozenges comprising a compound of formula (I) in a flavored base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of a compound of formula (I), which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a suitable buffer, for example, a glycine or citrate buffer, and rendering the resulting solution sterile and isotonic with the blood (pH range: 3.5-8.5). Injectable compositions according to the invention will generally contain about 0.5 mg/ml of active ingredient and may be diluted to a concentration of from 0.0001 to 0.05% w/v of active ingredient prior to administration. Parenteral administration is typically carried out at a rate of 0.001 ml/min/kg or more.

Compositions suitable for rectal administration are preferably presented as unit dose suppositories. These may be prepared by admixing a compound of formula (I) with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers which may be used include Vaseline, lanolin, polyethylene glycols, alcohols, and combinations of two or more thereof. The active compound is generally present at a concentration of from 0.001 to 1.0% w/w, for example, from 0.005 to 0.2% w/w.

Compositions for transdermal administration may be delivered by passive diffusion or by electrically-assisted transport, for example, iontophoresis (see, for example, Pharmaceutical Research 3(6), 318, (1986)) and may take the form of an optionally buffered aqueous solution of a compound of formula (I). Typical compositions comprise citrate or bis/tris buffer (pH 6) or ethanol/water containing from 0.1 to 0.2M active ingredient, but other compositions suitable for administration by transdermal iontophoresis are within the scope of the present invention.

For nasal administration, a particle size in the range 10-500 um is preferred to ensure retention in the nasal cavity. For pulmonary administration via the mouth, the particle size of the powder or droplets is typically in the range 0.5-10 um, preferably 1-5 um, to ensure delivery into the bronchial tree.

Metered dose inhalers are pressurized aerosol dispensers, typically containing a suspension or solution composition of the active ingredient in a liquefied propellant. During use these devices discharge the composition through a valve adapted to deliver a metered volume, typically from 10 to 150 ul, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The composition may additionally contain one or more co-solvents, for example, ethanol, surfactants, such as oleic acid or sorbitan trioleate or EXOSURF Neonatal ®, antioxidants and suitable flavoring agents.

EXOSURF Neonatal ® is a protein-free synthetic lung surfactant consisting if an aqueous suspension of colfosceril palmitate(dipalmitoylphosphatidylcholine), cetyl alcohol, tyloxapol(formaldehyde polymer with oxirane and 4-(1,1,3,3-tetramethylbutyl)phenol) and sodium chloride with the pH adjusted to a value of from 5 to 7.

Nebulizers are commercially available devices which transform solutions or suspensions of the active ingredient into a therapeutic aerosol mist either by means of acceleration of a compressed gas through a narrow venturi orifice, typically air or oxygen, or by mean of ultrasonic agitation. Suitable compositions for use in nebulizers consist of the active ingredient in a liquid carrier, the active ingredient comprising up to 40% w/w of the composition, but preferably less than 20% w/w. The carrier is typically water or a dilute aqueous alcoholic solution, preferably made isotonic with body fluids by the addition of, for example, sodium chloride. Other suitable carriers include surfactants, such as EXOSURF Neonatal ®. Optional additives include preservatives if the composition is not prepared sterile, for example, methyl hydroxybenzoate, antioxidants, flavoring agents, volatile oils, buffering agents and surfactants.

Suitable compositions for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant, for example, EXOSURF Neonatal ®. The active ingredient typically comprises from 0.1 to 100 w/w of the composition.

The compounds of the present invention are conveniently prepared by methods which are the same as or are analogous to those described in the aforementioned U.S. Pat. No. 4,306,075, which is incorporated in its entirety herein by reference.

For a better understanding of the invention, the following EXAMPLES ar given by way of illustration.

EXAMPLES

The cardiovascular effects of compound (A) were examined in animal models.
(a) Aortic blood pressure, heart rate and the Lead II ECG were recorded from 6 conscious beagles with indwelling cannulae. Compound (A) was given orally (0.1 and 0.5 mg/kg) or intravenously (0.3-3 ug/kg/min). Oral administration at 0.5 mg/kg, but not 0.1 mg/kg, resulted in significant hypotension. The maximum effect was observed within four minutes (mean fall: 42 mm Hg systolic, 31 mm Hg diastolic) and had recovered within 150 minutes of dosing. Heart rate was generally increased with a maximum change of 25 bpm. Intravenous infusions at doses ranging from 0.3-3 ug/kg/min resulted in a dose-dependent hypotension (falls of 12-45 mm Hg diastolic) accompanied by tachycardia.
(b) The model used was a open chest preparation of an anesthetized cat(anesthetic: chloralose and urethane).

A series of glysine buffer solutions of compound (A) were successively administered to each animal by i.v. infusion at doses equivalent to 100 ng, 300 ng, 1 ug, and 3 ug/kg/min. Each solution was infused over a period of 20 minutes, hypoxia being induced in the animal during the last 5 minutes of infusion by ventilating with 10% oxygen in nitrogen. A 15-minute 'recovery' period was observed between successive infusions. Following surgery, the animal was allowed to stabilize for 30 minutes, after which two 5-minute hypoxic challenges were given 15 minutes apart which were averaged to obtain the control hypoxic responses. 15 minutes after the second control hypoxic challenge, the animal started to receive the test compound. The averaged control hypoxic responses were compared with those obtained during infusion of the test compound.

Compound (A) was found to a potent pulmonary vasodilator in this model and markedly attenuated the pulmonary vasoconstriction induced by hypoxia. The overall acute beneficial hemodynamic effects observed were substantial reductions in pulmonary vascular resistance, pulmonary arterial pressure, systemic vascular resistance and mean arterial blood pressure and increases in cardiac output and stroke volume.

In another series of experiments, it was found that separate pretreatment of anesthetized dogs with enalapril (0.3 mg/kg), digoxin (100 mg/kg) and furosemide (1.0 mg/kg) 30–40 minutes prior to intravenous infusion of the compound of formula (A) respectively blocked, attenuated and potentiated the increase in Angiotensin II plasma concentration induced by the latter without significantly affecting its hemodynamic profile.

In yet another series of experiments, two anesthetized dogs were given a 20 ug/kg intratracheal bolus dose of the compound of formula (A), one as a solution in 5% ethanol/saline and the other as a solution in 5% ethanol/EXOSURF Neonatal ®. The plasma concentration of the compound of formula (A) was monitored for each animal and the mean terminal half-life determined in each case. The half-life of the EXOSURF-treated animal was found to be significantly longer than that of the saline-treated animal. Mean bioavailability with EXOSURF was 88% and without EXOSURF wa 46%.

TOXICITY

The compound of formula (A) was tested by oral and intravenous routes in acute and subchronic tests in mice, rates and dogs. These experiments established no effect levels and full reversibility was observed. Most effects were attributable to the known pharmacological activity of the compound of formula (A) which has a half-life measured in minutes for the species examined.

All of the effects observed in the animal models are desirable in the treatment of CHF.

PHARMACEUTICAL COMPOSITIONS
The active compound is the compound of formula (A).

| | mg per tablet |
|---|---|
| Instant Release Tablet | |
| Active Compound | 1 |
| Lactose | 79 |
| Microcrystalline Cellulose | 12 |
| Sodium Starch Glycollate | 4 |
| Povidone BP | 3 |
| Magnesium Stearate | 1 |
| | 100 |
| Instant Release Capsule | |
| Active Compound | 1 |
| Microcrystalline Cellulose | 20 |
| Pregelatinised Starch NF | 178 |
| Magnesium Stearate | 1 |
| | 200 |
| Controlled Release Tablet | |
| Active Compound | 5.0 |
| Lactose | 147.5 |
| Methocel K4M | 87.5 |
| Povidine K30 BP | 7.5 |
| Magnesium Stearate | 2.5 |
| | 250.0 |
| Intravenous Solution | |
| Disodium citrate solution, 0.1M | 0.6 ml |
| 0.1N NaOH solution | qs to pH 6 |
| Active Compound | 0.5 mg |
| Water for Injections | to 1 ml |
| Subcutaneous and Intramuscular Solution | |
| Disodium citrate solution, 0.1M | 0.5 ml |
| 0.1N NaOH solution | qs to pH 6.8 |
| Active Compound | 0.25 mg |
| Dextrose | 25 mg |
| Water for Injections | to 1 ml |

Transdermal Solution 0.01–0.2M solution of the active compound in a citrate or bis/tris buffer (pH 6) or ethanol/water.

What is claimed is:

1. A method of increasing the cardiac output and stroke volume of blood provided from the heart of a mammal identified as exhibiting congestive heart failure disorder having low cardiac output and stroke volume comprising the step of administering to said mammal an effective amount of the compound 9-deoxy-2',9-methano-3-oxa-4,5,6-trinor-3,7-(1'3'-interphenylene)-13,14-dihydro-prostaglandin $F_1$ to increase cardiac output and stroke volume of blood provided from said heart.

2. The method of claim 1 in which the compound is administered orally, parenterally or transdermally.

3. The method of claim 2 in which the compound is administered orally in a controlled release pharmaceutical preparation.

4. A method of increasing the cardiac output and stroke volume of blood provided from the heart of a mammal identified as exhibiting congestive heart failure disorder having low cardiac output and stroke volume comprising the step of administering to said mammal an effective amount of a physiologically acceptable base salt of the compound 9-deoxy-2',9-methano-3-oxa-4,5,6-trinor-3,7-(1'3'-interphenylene)-13,14-dihydro-prostaglandin $F_1$ to increase cardiac output and stroke volume of blood provided from said heart.

5. The method of claim 4 in which said salt is administered orally or parenterally.

6. The method of claim 5 in which said salt administered is the sodium salt.

7. The method of claim 4 in which said salt is administered transdermally.

8. The method of claim 7 in which the salt administered is the sodium salt.

* * * * *